United States Patent
Hashimoto et al.

[11] Patent Number: 6,152,951
[45] Date of Patent: Nov. 28, 2000

[54] METHOD OF TREATING CANCER

[75] Inventors: Yasuo Hashimoto, Yokohama; Toru Hirano, Hamamatsu; Noboru Yamaguchi, Yokohama, all of Japan

[73] Assignee: Hamamatsu Photonics K.K., Shizuoka-ken, Japan

[21] Appl. No.: 09/024,300

[22] Filed: Feb. 17, 1998

Related U.S. Application Data

[62] Division of application No. 08/380,616, Jan. 30, 1995, abandoned.

[30] Foreign Application Priority Data

Mar. 23, 1994 [JP] Japan ................................. 6-051950

[51] Int. Cl.⁷ ................................................ A61N 5/00
[52] U.S. Cl. ............................... 607/92; 607/88; 607/89; 606/15
[58] Field of Search .................. 606/10, 14–16; 607/88, 89, 90, 92, 93; 604/20–22

[56] References Cited

U.S. PATENT DOCUMENTS

| | | | |
|---|---|---|---|
| 4,592,353 | 6/1986 | Daikuzono | 128/303.1 |
| 4,693,244 | 9/1987 | Daikuzono | 128/303.1 |
| 4,740,047 | 4/1988 | Abe et al. | 350/96.15 |
| 4,889,129 | 12/1989 | Dougherty et al. | |
| 5,078,711 | 1/1992 | Kakami et al. | 606/16 |
| 5,129,896 | 7/1992 | Hasson | 606/15 |
| 5,163,935 | 11/1992 | Black et al. | 606/17 |
| 5,188,634 | 2/1993 | Hussein et al. | 606/15 |
| 5,190,536 | 3/1993 | Wood et al. | 606/16 |
| 5,222,953 | 6/1993 | Dowlatshahi | 606/15 |
| 5,409,483 | 4/1995 | Campbell et al. | 606/15 |
| 5,431,646 | 7/1995 | Vassiliadis et al. | 606/6 |
| 5,445,608 | 8/1995 | Chen et al. | 607/89 |
| 5,469,524 | 11/1995 | Esch et al. | 385/118 |
| 5,498,260 | 3/1996 | Rink et al. | 606/16 |
| 5,509,917 | 4/1996 | Cacchetti et al. | 606/15 |
| 5,514,125 | 5/1996 | Lasser et al. | 606/4 |
| 5,520,681 | 5/1996 | Fuller et al. | 606/17 |
| 5,571,099 | 11/1996 | Purcell, Jr. et al. | 606/17 |
| 5,733,277 | 3/1998 | Pallarito | 606/7 |

FOREIGN PATENT DOCUMENTS

| | | |
|---|---|---|
| 0 394 446 A1 | 10/1990 | European Pat. Off. |
| 0 441 040 A2 | 8/1991 | European Pat. Off. |

*Primary Examiner*—Linda C. M. Dvorak
*Assistant Examiner*—Bryan K. Yarnell
*Attorney, Agent, or Firm*—Kubovcik & Kubovcik

[57] ABSTRACT

There is provided a method of treating cancer. According to such a method, the affected tissue is irradiated effectively with activation light thereby obtaining an effect of the light treatment. The cancer therapeutic instrument used in the treatment method is equipped with a tube of which a tip is closed, a tip end of the tube being adapted to be inserted into a subject to be treated, and an optical fiber of which a tip end is adapted to be disposed slidably inside the tube.

7 Claims, 7 Drawing Sheets

METHOD OF TREATING CANCER

This application is a divisional of application Ser. No. 08/380,616, Jan. 30, 1995, now abandoned.

BACKGROUND OF THE INVENTION

1. Field of the Invention

The present invention relates to a cancer therapeutic instrument for use in treatment for cancers and neoplasm, and more particularly a cancer therapeutic instrument for use in treatment for the cancers originated, for example, in an area which involves a great deal of difficulty in performing a resection operation, the organs and the like, for instance, pancreatic carcinoma, lung cancer, brain tumor, cancers originated in the brain stem area, and for the cancers which are unfavorable to be resected from the point of view of beauty and maintenance of function, for example, breast cancer, head and neck cancer, tongue cancer and uterine cancer.

2. Description of the Related Art

Currently, cancer is one of the most terrible diseases which is left to mankind, and elucidation of its fundamental cause and therapy; and are in a developing state.

As typical therapy, which is considered at present to be effective, surgical resection, radiation therapy and chemotherapy are well known and most frequently employed.

Among those therapeutic methods, the surgical resection method is deemed to be most effective and is most frequently employed. On the other hand, for malignant tumors originated in the deep area of the body for which the surgical resection method cannot be employed, radiation therapy and chemotherapy are frequently used in combination. However, it often happens that both radiation therapy and chemotherapy involve strong adverse reaction, and the radiation therapy and chemotherapy are remarkably lower in complete cure rate in comparison with the surgical resection method and involve danger of relapses.

Recently, in view of the foregoing, there is hastened vigorously a study of cancer therapy according to physical therapy which involves no adverse reaction. As typical therapy, there are hyperthermia and phototherapy using a photosensitizer.

The hyperthermia is involved in a way such that a cancer cell is extinguished through heating and/or cooling thereof. It has been reported that keeping a cancer cell at a temperature, for example, higher by +5° C. than body temperature, which would cause merely relatively less damage to peripheral normal cells, throughout a definite time, alone may bring a great treatment effect.

On the other hand, the phototherapy is based on such a mechanism that irradiation with a specified wavelength of activation light on a cell absorbing a photosensitizer leads to an absorption of optical energy by the photosensitizer, so that activating oxygen, which will destroy the cell, emanates. This treatment utilizes the fact that an excretion ratio of the photosensitizer after injection thereof is extremely lower in a cancer cell in comparison with a normal cell, specifically, less than 1/3 (about 1/5).

The present invention is involved in the phototherapy, and thus the phototherapy will be described in detail hereinafter.

FIG. 9 is a graph showing a relation between time elapsed wherein a time point when an ATX-S10, which is one of photosensitizers, is injected into the body, is selected as a starting point and the relative concentrations of the ATX-S10 remaining in cells. The graph PN denotes the residual concentrations of the ATX-S10 within the normal cells; and the graph PC the residual concentrations of the ATX-S10 within the cancer cells.

When a certain standby time lapses (about 3 hours) after plenty of photosensitizer is injected into the affected part and its peripheral cells through a direct injection of the photosensitizer into the affected part, an intravenous injection and the like, the normal cells have discharged almost all the photosensitizer, whereas there appears such a state (light treatment feasible state) that almost all the photosensitizer stays in the cancer cells. In such a light treatment feasible state, irradiation with a specified wavelength of activation light leads to an emanation of activating oxygen, which will destroy the cells, within the cancer cells in which almost all the photosensitizer stays, while almost no activating oxygen emanates within the normal cells which have discharged almost all the photosensitizer, whereby the cancer cells are selectively extinguished.

Duration (the term of validity for light treatment) of the light treatment feasible state after an injection of the photosensitizer starts after 3 hours since injection of the photosensitizer and terminates after 14 hours with which the cancer cells have discharged almost all the photosensitizer. Incidentally, FIG. 9 shows an ATX-S10 by way of example. The standby time after injection of the photosensitizer and the term of validity for light treatment will vary about one order of magnitude in accordance with the type of photosensitizer.

The gist of this treatment resides in the point that activation light is continuously projected onto the affected part as uniformly as possible during the term of validity for light treatment, and the amount of irradiation light is controlled in such a manner that cell-inside-concentrations of activating oxygen which causes cells to be extinguished is restricted to a very low value such that the death rate of the normal cells is in the permitted limit within the normal cells, whereas the cell-inside-concentrations of activating oxygen assumes a value such that the death rate of the cancer cells is nearly 100% within the cancer cells.

To project the activation light onto the affected part, hitherto, an optical fiber is directly inserted into the affected part and activation light is transmitted through the optical fiber. However, according to this scheme:

(a) Since the optical fiber cannot be moved during the treatment, irradiation area or the therapeutic area is extremely limited;

(b) To project light from the tip of the optical fiber in all directions, it is necessary to cut the tip of the optical fiber, for example, in a cone shape. Processing for such an optical fiber is difficult and then the optical fiber is very expensive;

(c) To perform the treatment repeatedly, it is necessary to repeat insertion of the optical fiber whenever the treatment is performed. It is a great burden to both a patient and a doctor;

(d) Since the therapeutic area is narrow, it is difficult to cure completely large cancers and tumors; and (e) There are needs of sterilization of the optical fiber before use and re-sterilization of the optical fiber after each use or solid waste disposal. Usually, it is needed to provide an optical fiber having a length not less than 1 m, and the optical fiber is of a compound material. Consequently, the sterilization and the solid waste disposal are troublesome and thus the optical fiber is poor in operational efficiency.

SUMMARY OF THE INVENTION

In view of the foregoing, it is therefore an object of the present invention to provide a cancer therapeutic instrument capable of obtaining a great effect in light treatment through irradiation with activation light on the affected part over a wide range. The cancer therapeutic instrument is excellent in operational efficiency and is inexpensive.

To achieve the above-mentioned object of the present invention, according to the present invention, there is provided the first cancer therapeutic instrument comprising:

a catheter type of insertion member having a tube of which a tip is closed, a tip end of the tube being adapted to be inserted into a subject to be treated, and an optical fiber of which a tip end is adapted to be disposed slidably inside said tube;

a light source for emitting a predetermined activation light, said light source being arranged to introduce the activation light into said optical fiber so that the activation light travels within said optical fiber and emanates from a tip of said optical fiber at an end thereof in which said optical fiber is disposed inside said tube; and a driving mechanism for driving said optical fiber in such a manner that said optical fiber disposed inside said tube performs at least one movement selected from the group including reciprocation in a longitudinal direction of said tube and rotational motion using the longitudinal direction of said tube as a rotary axis.

Here, the terminology "tube of which a tip is closed" implies that it is acceptable either that the tip of the tube itself is closed, or that the tip of the tube is closed by a stopper or the like mounted in the opening of the tip.

In the first instrument according to the present invention, it is preferable that said optical fiber has at its tip an oblique plane with respect to the longitudinal direction of said optical fiber.

Further, it is preferable that said driving mechanism is arranged to drive said optical fiber so as to perform periodical reciprocation and/or rotational motion.

To achieve the above-mentioned object of the present invention, according to the present invention, there is provided the second cancer therapeutic instrument comprising:

a catheter type of insertion member having a tube of which a tip is closed, a tip end of the tube being adapted to be inserted into a subject to be treated, said tube being provided with a scatter member adapted to scatter a predetermined activation light, and an optical fiber of which a tip end is adapted to be disposed inside said tube, said optical fiber emitting from its tip the activation light toward said scatter member; and a light source for emitting the activation light, said light source being arranged to introduce the activation light into said optical fiber so that the activation light travels within said optical fiber and emanates from a tip of said optical fiber.

In the second instrument according to the present invention, it is preferable that said scatter member is made of plastic material containing polyacetal.

It is acceptable either that said scatter member is adapted to serve as a stopper for closing the tip of said tube as well, or that said scatter member is provided inside said tube of which the tip is closed.

Further, in the second instrument according to the present invention, it is preferable that said optical fiber has at the tip thereof a plane facing the longitudinal direction of said optical fiber, and said scatter member has at a position coming face to face with the tip of said optical fiber a plane expanding in parallel with said plane of said optical fiber.

To achieve the above-mentioned object of the present invention, according to the present invention, there is provided the third cancer therapeutic instrument comprising:

a catheter type of insertion member having a tube of which a tip is closed, a tip end of the tube being adapted to be inserted into a subject to be treated, and an optical fiber of which a tip end is adapted to be disposed inside said tube; and a light source for emitting a predetermined activation light, said light source being arranged to introduce the activation light into said optical fiber so that the activation light travels within said optical fiber and emanates from a tip of said optical fiber at an end thereof in which said optical fiber is disposed inside said tube, wherein when an emission solid angle, which indicates a spread of light emitted from said optical fiber, is defined as an area in which luminous density of emission light on a spherical surface given with a tip center of said optical fiber in the center becomes not less than 0.37 times a maximum, the tip of said optical fiber is formed as a plane with said emission solid angle being not less than 0.12 steradian.

In the third instrument according to the present invention, it is preferable that said optical fiber is adapted to be disposed slidably inside said tube, and said instrument further comprises a driving mechanism for driving said optical fiber in such a manner that said optical fiber disposed inside said tube performs a reciprocation in a longitudinal direction of said tube. In this case, it is preferable that said driving mechanism drives said optical fiber in such a manner that said optical fiber performs a periodical reciprocation.

In any of the first, second and third instrument according to the present invention, it is preferable that said tube is made of plastic material containing polyurethane or polyacetal, and in addition, it is preferable that said tube has, at an edge of the tip end which is inserted into the subject to be treated, a point which decreases in an area of a cutting plane perpendicular to the longitudinal direction of said tube with approaching the tip of said tube.

Further, in any of the first, second and third instrument according to the present invention, it is preferable that said light source is arranged to continuously or stepwise increase an incident light amount of said activation light entering said optical fiber with the passage of time.

According to the first cancer therapeutic instrument, the optical fiber is disposed slidably inside the tube. Thus, a patient does not feel pain even if the optical fiber is subjected to reciprocation or rotational motion. Further, insertion and drawing operations of the optical fiber involve no danger such that a patient is damaged every operation. Hence, it is facilitated that treatment is performed on a divisional basis into a plurality of number of times. Incidentally, it is permitted to use tubes with a diameter of the order of 0.5 mm–1.5 mm, and there is little side effect such as the bleeding or the like due to inserting the tube into the affected part.

It is sufficient that the strict sterilization of the optical fiber before use or treatment is performed for only the tube. Further, after the treatment it is possible to easily perform solid waste disposal for the tube, which is much more inexpensive than the optical fiber, by means of, for example, burning the tube. And in addition, the first cancer therapeutic instrument is excellent in operational efficiency.

Further, reciprocating the optical fiber makes it possible to obtain a broad irradiation area in the longitudinal direction of the tube, thereby coping with a large affected part.

To cut obliquely the tip of the optical fiber is implemented inexpensively, and combined with the use of rotational motion the oblique cut of the optical fiber makes it possible to obtain a broad irradiation area around the tube.

Periodical reciprocation and/or rotational motion of the optical fiber makes it possible to continuously irradiate with activation light for a long time throughout a broad light irradiation area, and in addition makes it possible to prevent fusion and carbonization of a thin tube due to the heat of light irradiation, thereby enabling the use of the tube for a long time, since it does not happen that a specified portion of the tube is continuously irradiated with light.

According to the second cancer therapeutic instrument, a scatter member is provided inside a tube. Such an instrument is suitable for treatment of a small affected part. The use of such a scatter member makes it possible, with out reciprocation and/or rotational motion of the optical fiber, but in a simple way, to form the tip of the optical fiber as a light source which may emit light beams in all directions, most suitable for treatment. It is possible for the scatter member to be formed of a plastic material containing, for example, polyacetal, which also can be used to form the tube, and is inexpensive. It is acceptable either that the scatter member is adapted to serve as a stopper for the tip of the tube as well; that the tip of the tube is originally made in such a configuration that the scatter member is disposed; that the scatter member is inserted from the tip having an opening and thereafter the opening is closed; or that the scatter member is inserted from the rear end of the tube having an opening into the tube. In a case where the scatter member is provided, there is no need to cut obliquely the tip of the optical fiber, and it is acceptable that the optical fiber has at the tip thereof a plane having a cut perpendicular to the longitudinal direction of the optical fiber, and said scatter member has at a position coming face to face with the tip of said optical fiber, a plane expanding in parallel with said plane of the optical fiber.

According to the third cancer therapeutic instrument, the tip of an optical fiber, which is disposed inside a tube, is equipped with a scatter plane so that activation light is emitted from the tip of the optical fiber with a spread not less than a predetermined solid angle.

In the third cancer therapeutic instrument, the reason why when an emission solid angle, which indicates a spread of light emitted from the optical fiber, is defined as an area in which luminous density of emission light on a spherical surface given with a tip center of the optical fiber in the center becomes not less than 0.37 times a maximum, the scatter plane of the tip of said optical fiber is defined as a plane with said emission solid angle being not less than 0.12 steradian, is that such a degree of scatter plane can be obtained simply and inexpensively through rough grinding by a file and the like, and that a broad area of the affected part is irradiated with activation light so that an effect of treatment can be obtained, through the spread of activation light to such an extent that the above definition is satisfied, even if an independent scatter member or the like is not provided in addition to the optical fiber.

In the third cancer therapeutic instrument of the present invention, when the optical fiber is slidably disposed inside the tube and is reciprocated, it is possible to obtain a broader light irradiation area, thereby coping with a large affected part. Further, providing a periodical reciprocation permits a broad light irradiation area to be uniformly irradiated with activation light.

In any of the first, second and third cancer therapeutic instruments of the present invention as described above, as main raw materials for the tube, if polyurethane or polyacetal is selected, it is possible to provide a tube having a light transmission ability which is necessary for the therapeutic instruments, and having a soft structure which involves no danger such that the human body is damaged, the tube being free from toxicity for the human body. Further, in case of polyacetal, this involves such an advantage that it is hard to be carbonized even if the tube is irradiated with strong light.

Further, sharpening the tip of the tube facilitates the tube to be inserted into the affected part.

As shown in FIG. 9, even in effective period of light treatment, concentrations of photosensitizer within the normal cells continue to be decreased, and thus activating oxygen is hardly produced within the normal cells even with irradiation of strong activation light. Consequently, it is possible to obtain the further effect of treatment through irradiation with stronger activation light with the passage of time.

According to any of the first, second and third cancer therapeutic instruments of the present invention as described above, it is possible to provide inexpensively tubes and optical fibers capable of withstanding the use for a long time and also obtaining a broad light irradiation area. Further, it is excellent in operational efficiency and in sanitary management since only the tube, which is inexpensive and can be disposed of by burning, may be used on a throw-away basis for each patient or each treatment.

DESCRIPTION OF THE PREFERRED EMBODIMENTS

Hereinafter, there will be described embodiments of the present invention.

Figure 1:
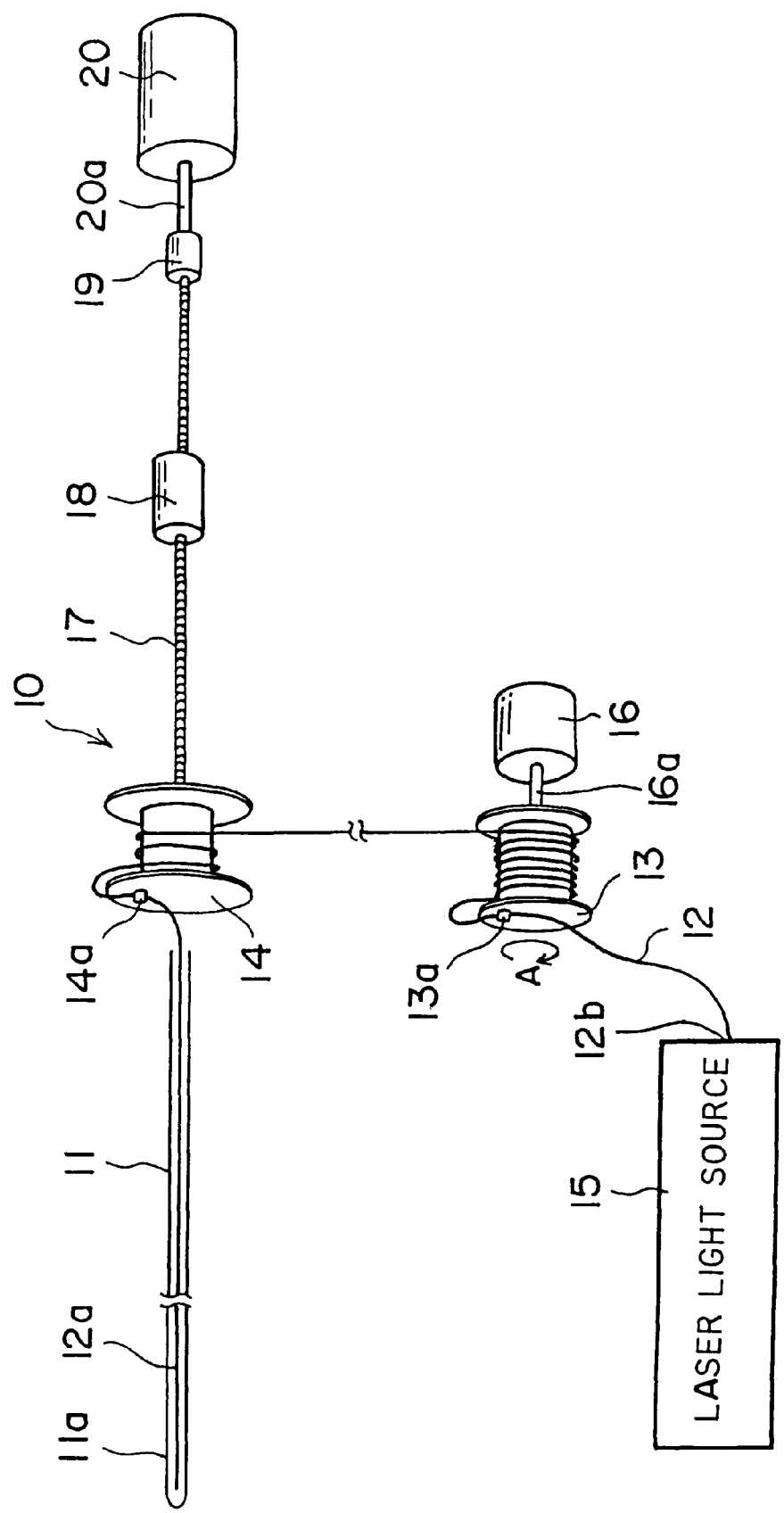
FIG. 1 is a typical illustration of a cancer therapeutic instrument according to an embodiment of the present invention.

FIG. 1 is a typical illustration of a cancer therapeutic instrument according to an embodiment of the present invention.

In FIG. 1, the cancer therapeutic instrument 10 is equipped with a throw-away type of tube 11 the tip portion 11a of which is inserted into the affected part involved in the cancer or the tumor within the body of the patient. The tube 11 is made of, for example, polyacetal and is of a diameter of the order of about 1 mm.

The cancer therapeutic instrument 10 is further equipped with an optical fiber 12 which is wound into a first reel 13 and a second reel 14 and is fixed on the first reel 13 and the second reel 14 through fixtures 13a and 14a, respectively. The tip portion 12a of the optical fiber 12 at the end of the second reel 14 is inserted into the tube 11 and reaches the tip portion 11a. An incident end 12b of the optical fiber 12 is connected to a laser light source 15. The laser light source 15 emits a beam of laser light having a wavelength utilized as the activation light. The emitted beam of laser light is introduced to the optical fiber 12 through the incident end 12b of the optical fiber 12. The laser light source 15 can emit laser light which is variable in a quantity of light. The quantity of light is varied with the passage of time by a control circuit (not illustrated). Details will be described later. The laser beam introduced to the optical fiber 12 travels through the optical fiber 12 and emanates from the tip inserted into the tube 11.

The first reel 13 is coupled with a shaft 16a of a torque motor 16 so as to be actuated in an arrow direction A shown in the figure. Fixed on the second reel 14 is a rod 17 over the surface of which male screws are formed. The rod 17 is engaged with a fixed bearing 18 on a spiral basis, and is coupled through a coupling member 19 to a shaft 20a of a reversible motor 20. The fixed bearing 18 is fixed on a base or the like (not illustrated). The reversible motor 20 is rotatable both forward and backward. Providing a guide member (not illustrated) prevents the motor main body from being rotated, and permits the motor to overall move forward and backward (left and right in the figure).

When the reversible motor 20 rotates forward, the rod 17 also rotates forward. Thus, since the rod 17 is engaged with the fixed bearing 18 on a spiral basis, the rod 17 moves forward together with the reversible motor 20, so that the second reel 14 is rotated and advanced. At that time, the second reel 14 pulls the optical fiber 12 wound into the first reel 13 so as to be wound into the second reel 14. Whereas the tip portion 12a of the optical fiber 12 is squeezed into the tube 11, while the optical fiber 12 is rotated forward using a longitudinal direction of the optical fiber 12 as an axis. On the other hand, when the reversible motor 20 rotates backward, the rod 17 also rotates backward and steps back. As a result, part of the optical fiber 12, which has been wound into the second reel 14, is rewound into the first reel 13, so that the tip portion 12a of the optical fiber 12 rotates reversely and moves in such a direction that it is drawn from the tube 11. The control circuit (not illustrated) for controlling the reversible motor 20 is provided with a timer. The reversible motor 20 switches over repeatedly the forward rotation and the backward rotation whenever the timer counts up, whereby the tip portion 12a of the optical fiber 12 repeats periodical reciprocation and rotational motion within the tube 11.

Incidentally, according to the present embodiment as described above, there is shown an example in which both the reciprocation and the rotational motion are applied to the tip portion 12a of the optical fiber 12. However, it is noted that modifications can be made. For example, if the fixed bearing 18 is removed and the reversible motor 20 is fixed, the tip portion 12a of the optical fiber 12 performs only the rotational motion. Further, if the fixed bearing 18 is removed, and in addition the rod 17 is coupled with the tip portion 12a of the optical fiber 12 through a gear assembly or the like, with which the coupling member 19 is replaced, for converting the rotational motion of the shaft 20a of the reversible motor 20 into the linear motion, it is possible to provide for the tip portion 12a of the optical fiber 12 only the reciprocation in the longitudinal direction of the tube.

To use the cancer therapeutic instrument 10 shown in FIG. 1, photosensitizer is injected into the affected part, the tube 11 is inserted into the affected part, the tip portion 12a of the optical fiber 12 is inserted into the tube 11, and operation is initiated after a predetermined standby time lapses.

Figure 2:
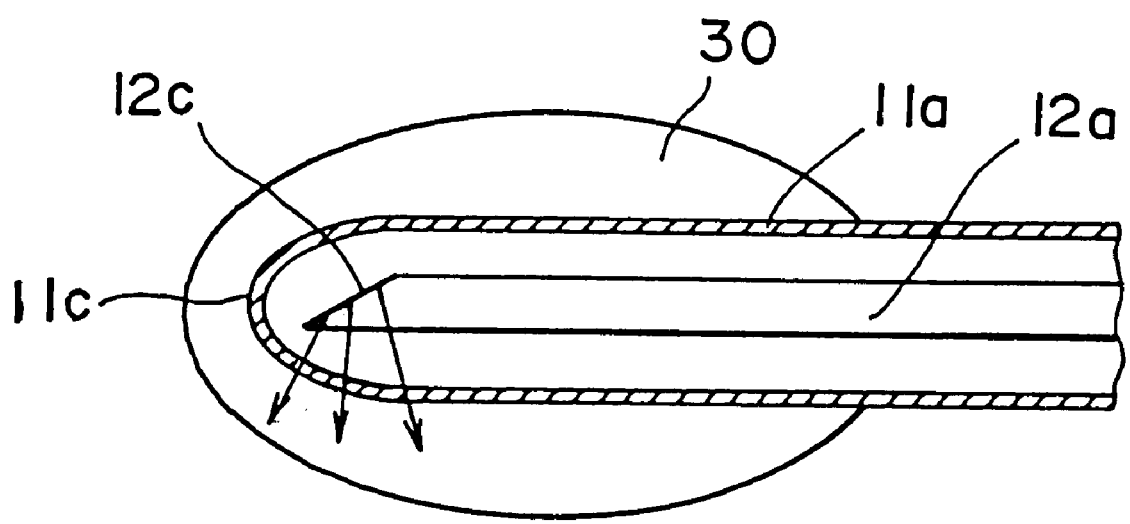
FIG. 2 is a partially enlarged view showing the tip portion of a tube inserted into the affected part and the tip portion of an optical fiber inserted into the tube.

FIG. 2 is a partially enlarged view showing the tip portion 11a of the tube 11 inserted into the affected part 30 and the tip portion 12a of the optical fiber 12 inserted into the tube 11.

As seen from FIG. 2, the tip 11c of the tip portion 11a of the tube 11 is closed so as to prevent body fluids from invading the inside. The tip of the tip portion 12a of the optical fiber 12, which is inserted up to the tip portion 11a of the tube 11, is provided with the tip plane 12c formed by cutting the tip obliquely as shown in the figure. The laser beam that has traveled through the inside of the optical fiber 12 is reflected by the tip plane 12c and is emitted through the side surface of the tube 12, so that the affected part 30 is irradiated with the laser beam emitted through the side surface of the tube 12.

Figure 3A:
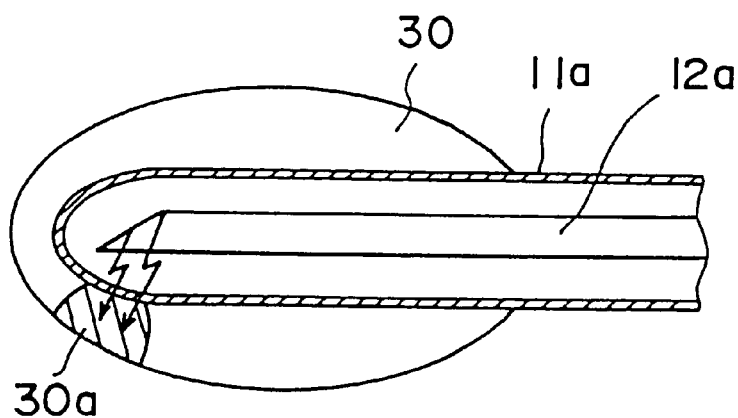
FIGS. 3(A)–3(C) are each a view useful for understanding a variation of irradiation area of laser beams according to movement of the optical fiber.
Figure 3B:
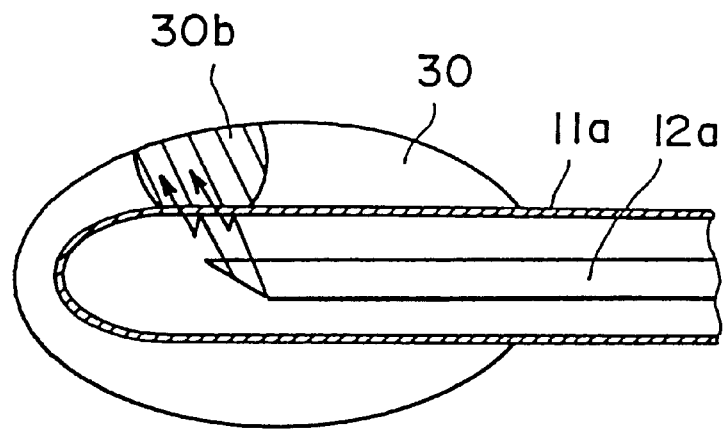
Figure 3C:
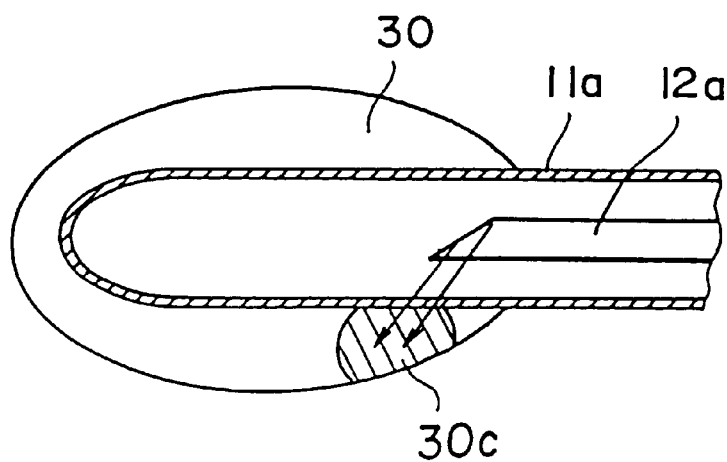

FIGS. 3(A)–3(C) are each a view useful for understanding the variation of irradiation area of laser beams according to movement of the optical fiber.

In a state shown in FIG. 3(A), a partial area 30a of the affected part 30 is irradiated with the laser beam. In this state, the tip portion 12a of the optical fiber 12 is rotated and moved in such a direction that it is drawn from the tube 11. At that time, another partial area 30b of the affected part 30 is irradiated with the laser beam as shown in FIG. 3(B). When the tip portion 12a of the optical fiber 12 is rotated and moved to assume the state shown in FIG. 3(C), additional partial area 30c of the affected part 30 is irradiated with the laser beam. In this manner, reciprocation and rotation of the tip portion 12a of the optical fiber 12 inside the tube 11 permits the affected part 30 to be repeatedly irradiated with the laser beams throughout the affected part 30 uniformly.

Figure 4:
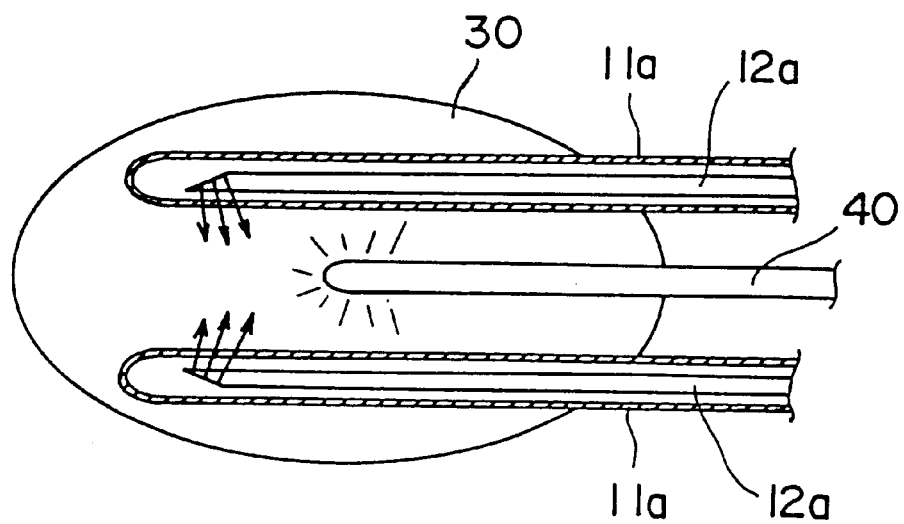
FIG. 4 is a view showing a state in which two tubes are inserted into the affected part, and in addition a heat pipe is inserted into the affected part.

FIG. 4 is a view showing a state in which two tubes 11 are inserted into the affected part 30, and in addition a heat pipe 40 is inserted into the affected part 30.

In a case where the affected part 30 is large, it is acceptable to provide such an arrangement that a plurality of tubes 11 are inserted as shown in the figure, a plurality of optical fibers 12 emit laser beams, and the affected part 30 is irradiated with the laser beams throughout with the performance of only one treatment. The continuous irradiation with the laser beams heats the affected part 30. If it is desired to lower the temperature of the affected part 30, it is acceptable that the heat pipe 40 is inserted into the affected part 30 as shown in the figure to cool the affected part 30. Alternatively, it is also acceptable to further heat the affected part 30 through the heat pipe 40 so that the above-mentioned hyperthermia is used in combination with the phototherapy.

Figure 5:
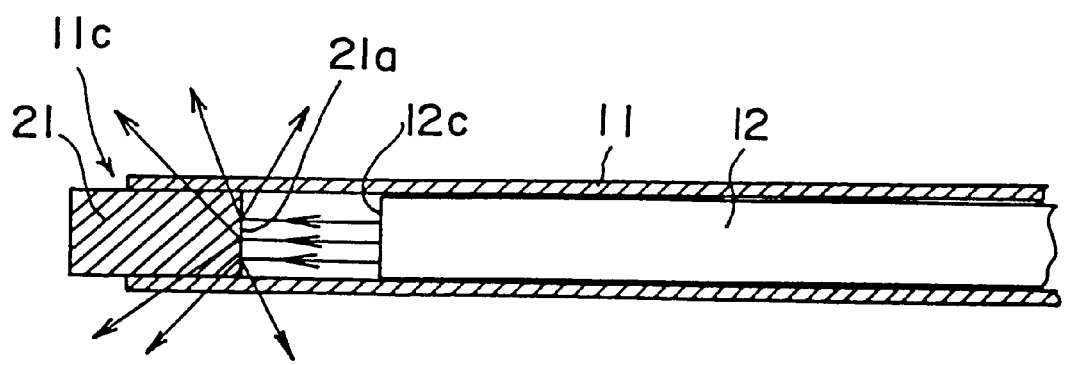
FIG. 5 is a partially enlarged view showing the tip portion of a tube and the tip portion of an optical fiber according to another embodiment of a cancer therapeutic instrument of the present invention.

FIG. 5 is a partially enlarged view showing the tip portion of a tube and the tip portion of an optical fiber according to another embodiment of a cancer therapeutic instrument of the present invention.

The tip 11c of the tube 11 opens in the end. A scatter member 21 is mounted in the opening of the tip 11c of the tube 11 and fixed thereon. The scatter member 21 serves as a stopper with which the opening is closed up. Both the scatter member 21 and the tube 11 are each made of polyacetal. The optical fiber 12 is inserted inside the tube 11. It is preferable that the optical fiber 12 is feasible in insertion into and drawing from the tube 11. However, during the treatment, the optical fiber 12 is disposed at a predetermined position inside the tube 11, and is not moved and rotated.

The tip plane 12c of the optical fiber 12 is cut perpendicularly. The rear end 21a of the scatter member 21 is formed to come face to face with the tip plane 12c of the optical fiber 12, so that part of the laser beams emitted from the tip plane 12c of the optical fiber 12 is reflected on the rear end 21a of the scatter member 21 and then projected from the tube 11, and the other part is projected through the inside of the scatter member 21 from the side of the tube or the tip of the scatter member 21. With such a simple structure, there is realized a non-directional light source which is capable of projecting the laser beams from the tip in all directions. This light source is available to project the laser beams in all directions in such a state that the tube is inserted into the affected part, and the optical fiber is inserted into the tube and is rested. Such a light source is effective particularly in a case where the affected part is small.

Figure 6:
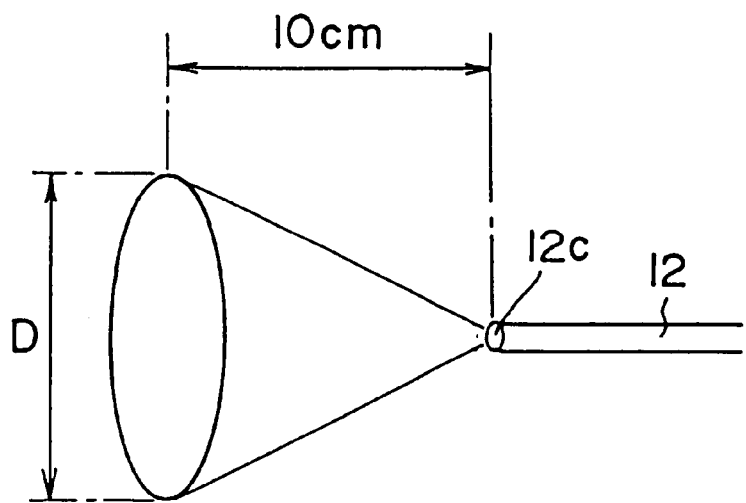
FIG. 6 is a view showing the tip portion of an optical fiber and the state of spread of emitted light according to still another embodiment of a cancer therapeutic instrument of the present invention.

FIG. 6 is a view showing the tip portion of an optical fiber and the state of spread of emitted light according to still another embodiment of a cancer therapeutic instrument of the present invention.

While the tip plane 12c of the optical fiber 12 is cut perpendicularly, the tip plane 12c is subjected to rough grinding by a file. Thus, the laser beam emitted from the tip plane 12c is projected as being spread so that a beam of light at the position advanced by 10 cm from the tip plane 12c is given with its diameter $D \geqq 2$ cm.

In this manner, the optical fiber 12, of which the tip plane 12c is processed so that the laser beam is projected as being spread, is inserted into the tube and the affected part is irradiated with the laser beam with the optical fiber 12 rested if the affected part is small, whereas while the optical fiber 12 is reciprocated if the affected part is large.

Figure 7A:
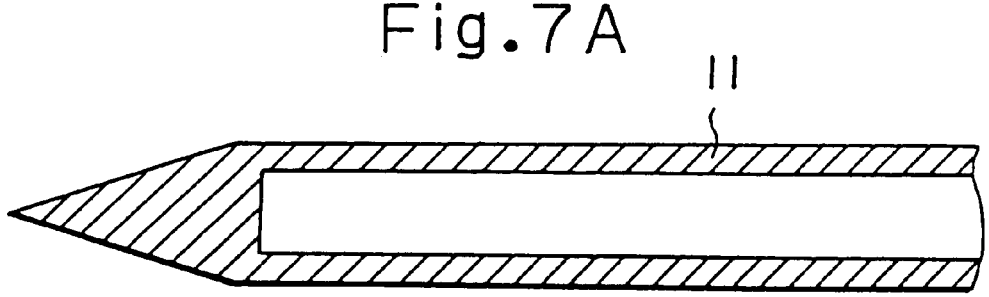
FIGS. 7 (A) and (B) are each a view showing the tip of a tube.
Figure 7B:
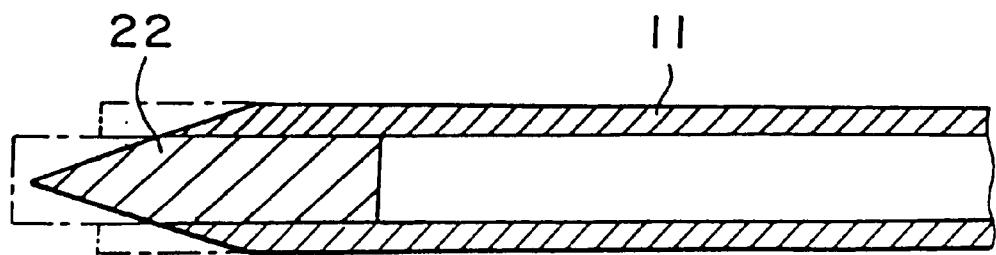

FIGS. 7 (A) and (B) are each an enlarged view showing the tip of a tube.

In FIG. 7 (A), the tip portion of the tube 11 of which the tip is closed is processed in a pin shaped sharp configuration. In FIG. 7 (B), a stopper is mounted in the tip portion of the tube 11 of which the tip is opened, and the tip portion including the stopper is processed in a pin shaped sharp configuration. Incidentally, it is noted that the dashed lines in FIG. 7 (B) show the configuration before processing. In this manner, providing sharpness of the tip portion of the tube 11 makes it possible to smoothly insert the tube 11 into the affected part.

Incidentally, there is no need to sharpen the tip portion of the tube 11 to form a cone. It is sufficient that; and inexpensive processing way such as a simple oblique cut, a triangular pyramid—like shaped cut and the like is adopted.

Figure 8:
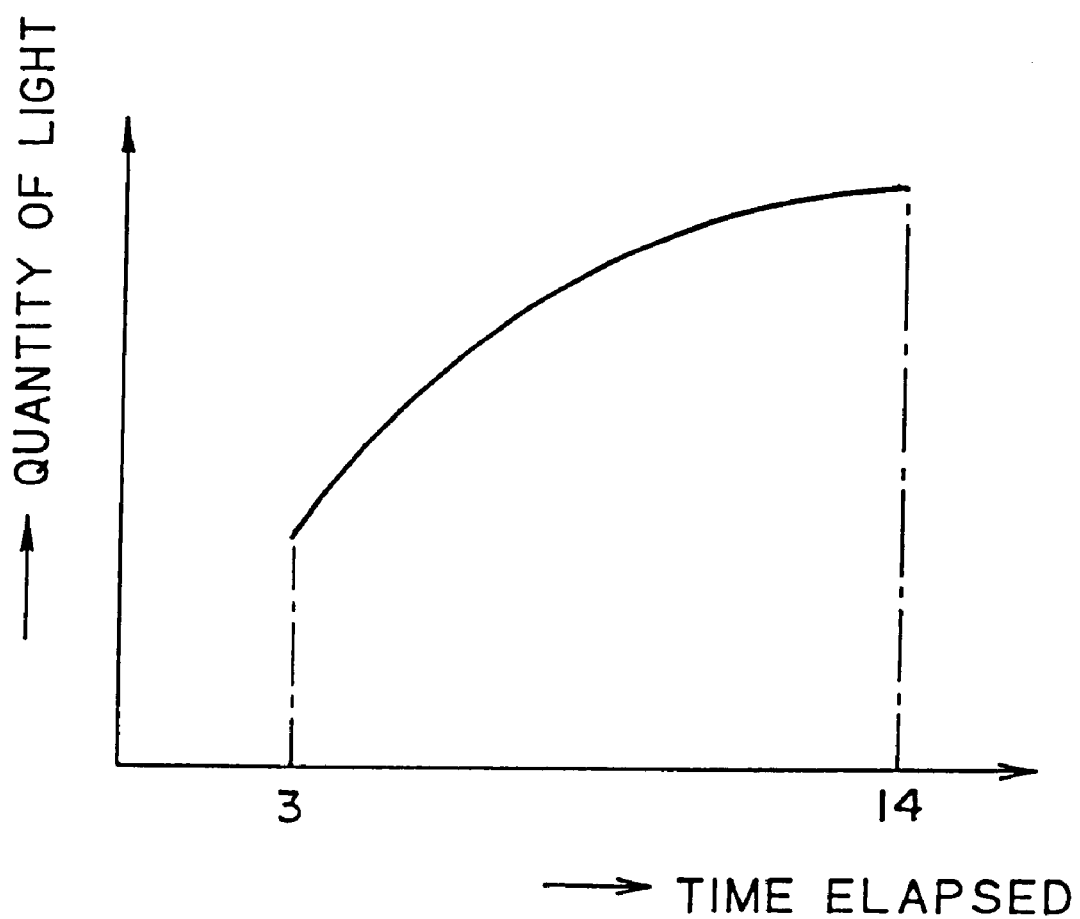
FIG. 8 is a graph which exemplarily shows a variation of an amount of light emitted from a laser light source according to time elapsed.

FIG. 8 is a graph which exemplarily shows the variation of an amount of light emitted from a laser light source 15 (cf. FIG. 1) according to time elapsed.

Figure 9:
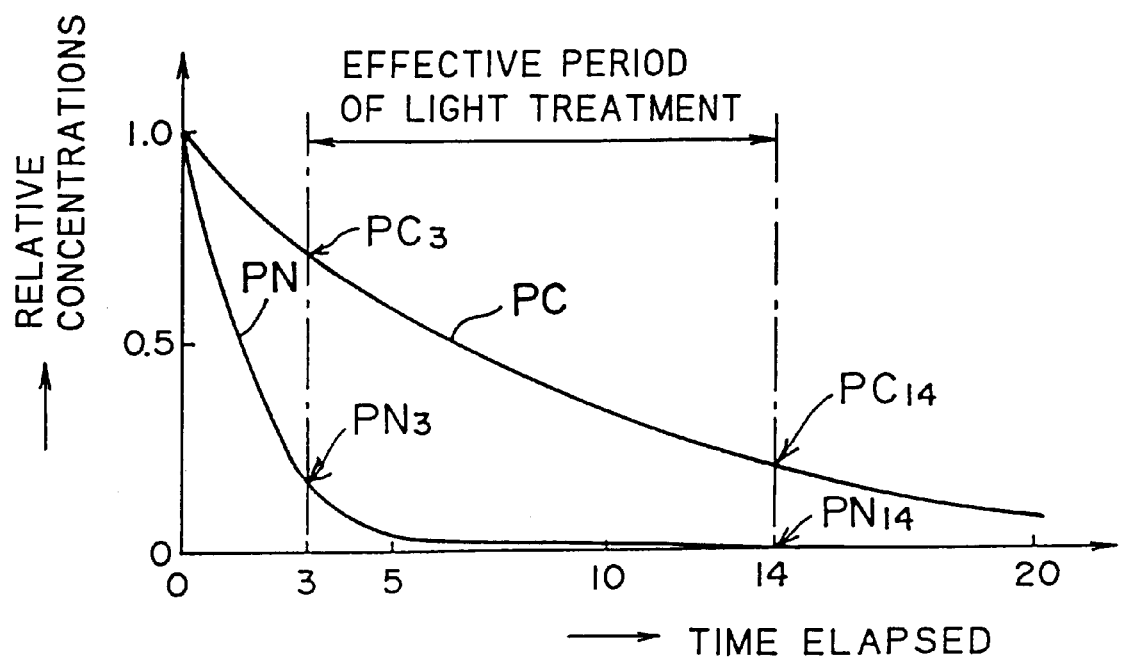
FIG. 9 is a graph showing a relation between time elapsed wherein a time point when photosensitizer is injected into the body is selected as a starting point and the relative concentrations of the photosensitizer remaining in cells.

In the first stage of an effective period of light therapy shown in FIG. 9, some measure of photosensitizer will still remain also in the normal cells. Thus, light beams emanate with a relatively slight quantity of light at first, and thereafter the quantity of light is increased as the photosensitizer is excreted from the normal cells according to time elapsed. This control makes it possible to obtain the maximum effect in treatment, limiting harm or damage to normal cells to a minimum.

As described above, according to the present invention, it is possible to obtain a great effect in the phototherapy through effective irradiation with activation light on the affected part, and in addition to implement a cancer therapeutic instrument which is capable of reducing the burden to a patient and is excellent in safety and sanitation since there is provided a throw-away type of tube.

While the present invention has been described with reference to the particular illustrative embodiments, it is not to be restricted by those embodiments but only by the appended claims. It is to be appreciated that those skilled in the art can change or modify the embodiments without departing from the scope and spirit of the present invention.

What is claimed is:

1. A method of treating cancer comprising:

injecting a photosensitizer into a part of a body affected with cancer;

providing a cancer therapeutic instrument comprising:

a source of laser light;

a thin tube having an open end and a closed end and having a substantially uniform diameter along its entire length, said tube being formed of a material that transmits light, said closed end of said tube being configured such that said tube can be inserted into a subject to be treated;

an optical fiber having first and second ends, said first end being slidably disposed within said tube and said second end being connected to said light source; and a driving mechanism comprising a motor and connected to said optical fiber, said mechanism being capable of moving said optical fiber within said tube by reciprocating said optical fiber along a longitudinal axis of said tube and by rotating said optical fiber;

inserting the closed end of said tube into said affected part; and irradiating said affected part with said laser light by simultaneously and continuously rotating and reciprocating said optical fiber along an axis of said tube adjacent said affected part.

2. The method of treating cancer of claim 1, wherein the first end of the optical fiber is cut so as to define an oblique plane relative to a longitudinal axis of the optical fiber.

3. The method of treating cancer of claim 1, wherein the driving mechanism reciprocates or rotates the optical fiber at periodic intervals.

4. The method of treating cancer of claim 1, wherein the closed end of the tube has a sharp tip thereon to facilitate insertion of the tube into the subject to be treated.

5. The method of treating cancer of claim 1, wherein the tube is comprised of a plastic material containing polyacetal.

6. The method of treating cancer of claim 1, wherein the light source is controlled such that the light intensity therefrom increases with the passage of time.

7. A method of treating cancer comprising:

injecting a photosensitizer into cancerous cells of a subject to be treated;

inserting a catheter tube having a substantially uniform diameter along its length and having a closed distal end into said subject in a part affected with said cancerous cells;

slidably disposing an optical fiber into said catheter tube, said optical fiber having a tip end for emanating laser light; and emanating a predetermined activation light from said tip end of said optical fiber and simultaneously and continuously rotating and reciprocating said optical fiber along an axis of said tube adjacent said affected part so as to irradiate said cancerous cells.

* * * * *